US012090029B2

(12) United States Patent
Yeung et al.

(10) Patent No.: US 12,090,029 B2
(45) Date of Patent: Sep. 17, 2024

(54) DEVICES AND METHODS FOR ENHANCING IMMUNOGENICITY TO INTRADERMAL VACCINATION

(71) Applicant: VERSITECH LIMITED, Telegraph Bay (HK)

(72) Inventors: Raymond Hung To Yeung, Aberdeen (HK); Wing Yan Lau, Sai Wan Ho (HK); Fan Ngai Hung, Mid-Level (HK); Johnson Yiu-Nam Lau, Houston, TX (US); Kwok Yung Yuen, Pokfulam (HK)

(73) Assignee: VERSITECH LIMITED, Hong Kong (CN)

( * ) Notice: Subject to any disclaimer, the term of this patent is extended or adjusted under 35 U.S.C. 154(b) by 788 days.

(21) Appl. No.: 16/348,287

(22) PCT Filed: Nov. 8, 2017

(86) PCT No.: PCT/US2017/060709
§ 371 (c)(1),
(2) Date: May 8, 2019

(87) PCT Pub. No.: WO2018/089542
PCT Pub. Date: May 17, 2018

(65) Prior Publication Data

US 2019/0321234 A1 Oct. 24, 2019

Related U.S. Application Data

(60) Provisional application No. 62/419,895, filed on Nov. 9, 2016.

(51) Int. Cl.

| | |
|---|---|
| ***A61F 13/00*** | (2024.01) |
| ***A61F 13/02*** | (2006.01) |
| ***A61F 17/00*** | (2006.01) |

(52) U.S. Cl.
CPC .... *A61F 13/0233* (2013.01); *A61F 13/00063* (2013.01); *A61F 17/00* (2013.01)

(58) Field of Classification Search
CPC ...................................................... A61F 17/00
(Continued)

(56) References Cited

U.S. PATENT DOCUMENTS 2,221,758 A * 11/1940 Elmquist .......... A61F 13/00021 128/888
5,008,110 A 4/1991 Benecke
(Continued)

FOREIGN PATENT DOCUMENTS

CN 102949779 A * 3/2013

OTHER PUBLICATIONS

Allison, A.C., Squalene and squalane emulsions as adjuvants, https://pubmed.ncbi.nlm.nih.gov/10525443/, 1999 (Year: 1999).*
(Continued)

*Primary Examiner* — Kim M Lewis
(74) *Attorney, Agent, or Firm* — PABST PATENT GROUP LLP

(57) ABSTRACT

Devices and methods that utilize an occlusive dressing in combination with a topical pharmaceutical agent to enhance vaccine efficacy are described. The occlusive dressing delivers a defined dose of a topical pharmaceutical agent that enhances immune system reactivity to a vaccine to the site of vaccination, and provides a barrier that maintains a layer of the topical pharmaceutical agent on the skin for a desired period to time while also providing a port through which an immunizing composition can be administered. In some embodiments the occlusive dressing includes a wound dressing for covering the injection site following vaccination.

16 Claims, 9 Drawing Sheets

(58) Field of Classification Search
USPC ............ 128/888, 829; 604/180, 192; 602/48
See application file for complete search history.

(56) References Cited

U.S. PATENT DOCUMENTS

| | | | | |
|---|---|---|---|---|
| 5,086,763 | A * | 2/1992 | Hathman | A61F 13/0246 128/887 |
| 8,403,899 | B2 | 3/2013 | Sherman | |
| 8,641,689 | B2 | 2/2014 | Messier | |
| 2003/0153861 | A1 * | 8/2003 | Royer | A61F 13/023 602/54 |
| 2004/0137004 | A1 * | 7/2004 | Glenn | A61K 9/7061 424/184.1 |
| 2004/0138602 | A1 * | 7/2004 | Rossen | A61F 13/0226 602/41 |
| 2004/0158186 | A1 * | 8/2004 | Hall | A61F 13/0203 602/48 |
| 2005/0176084 | A1 | 8/2005 | Burkoth | |
| 2009/0060928 | A1 * | 3/2009 | Bystryn | A61K 39/39 424/184.1 |
| 2010/0104673 | A1 * | 4/2010 | Tecco | A61K 8/676 514/23 |
| 2014/0296826 | A1 * | 10/2014 | Finke | A61L 15/46 604/506 |
| 2018/0015050 | A1 * | 1/2018 | Olivero | A61K 9/0014 |
| 2018/0318139 | A1 * | 11/2018 | Stavrou | A61F 7/02 |

OTHER PUBLICATIONS

CN-102949779-A, translation. (Year: 2013).*

PCT Search Report & Written Opinion dated Feb. 19, 2018 for PCT/US2017/060709 filed on Nov. 8, 2017 in the name of EMV Enhance (HK) Limited & Versitech Limited entitled Devices and Methods for Enhancing Immunogenicity to Intradermal Vaccination.

* cited by examiner

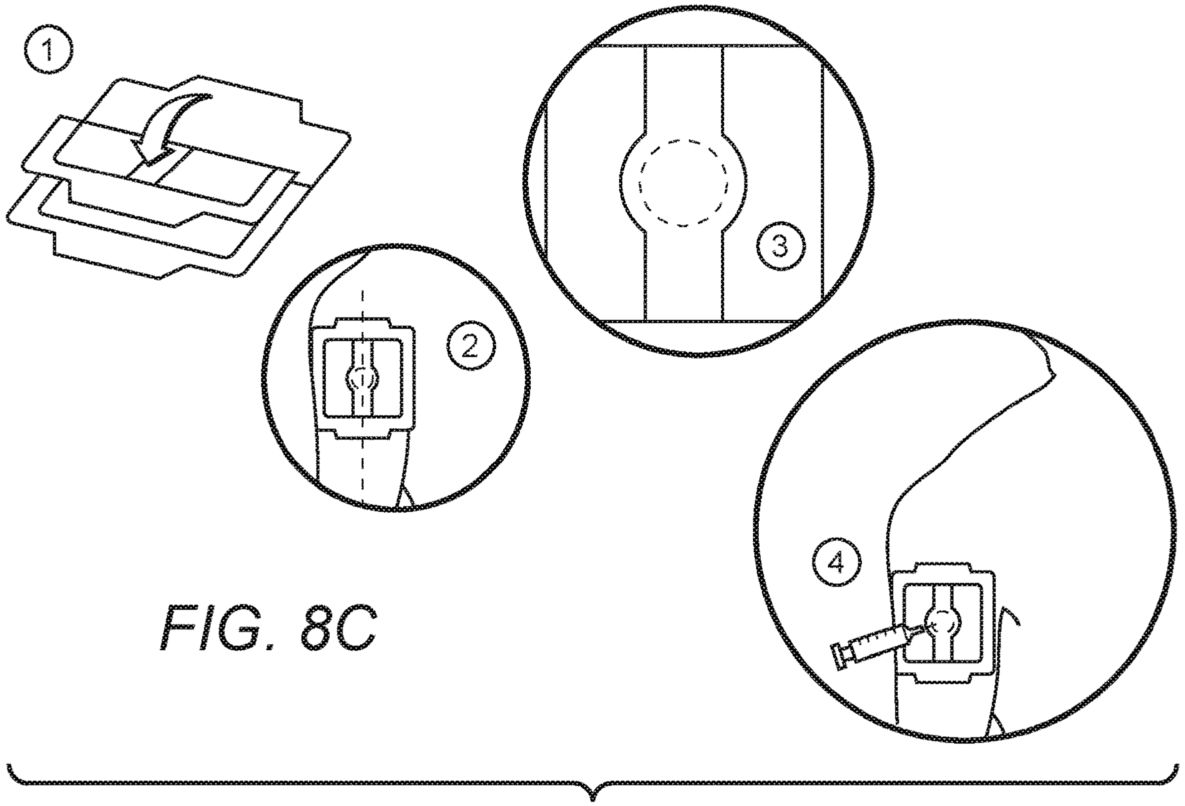
FIG. 8C
FIG. 9
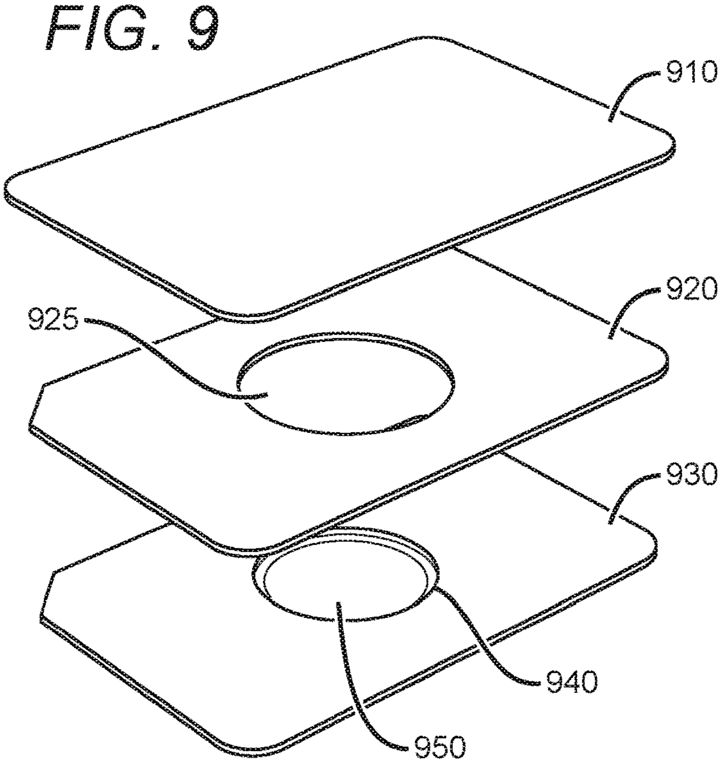

DEVICES AND METHODS FOR ENHANCING IMMUNOGENICITY TO INTRADERMAL VACCINATION

This application claims the benefit of U.S. Provisional Application No. 62/419,895 filed on Nov. 9, 2016. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is devices and methods for enhancing the effectiveness of intradermally applied vaccines, in particular influenza vaccines.

BACKGROUND

The background description includes information that may be useful in understanding the present invention. It is not an admission that any of the information provided herein is prior art or relevant to the presently claimed invention, or that any publication specifically or implicitly referenced is prior art.

Annual epidemics and pandemics of influenza (flu) cause significant disease burden and excess mortality due to complications globally. Vaccination with flu vaccine is considered to be the most effective way to alleviate disease burden and mortality caused by influenza, as well as to prevent further pandemic in humans. Several preparations of influenza vaccines are currently available, including the inactivated influenza whole-virus vaccine, virion-free "split" virus or subunit vaccine, recombinant hemagglutinin (HA) vaccine, and live attenuated influenza virus vaccine (Centre for Disease Control and Prevention 2013). All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Commercial flu vaccines can have low immunogenicity and may not be ready within a short timeframe in response to rapidly emerging flu strains. Poor immunogenicity is well known for commercial vaccines, and particularly impacts older adults and young children. Meta-analysis estimated that the overall efficacy of these vaccines is around 70% (Osterholm et al., 2012). These problems have limited the benefits of flu vaccines for the elderly and young population, which are at the high risks of hospitalization for influenza infection and its complications, and needs the vaccine protection most.

Recently, attempts have been employed to improve vaccine immunogenicity, including vaccination via the intradermal route (Huang 2012a; Huang 2012b) and administration of new vaccine adjuvants derived by recruiting the functions of the pattern recognition receptors (PRRs) in the innate immune system, including the Toll-like receptors (TLRs), retinoic acid-inducible gene-like receptors, and NOD-like receptors (Kasturi et al., 2011; Pashine et al., 2005; Demento et al., 2009). For example, imiquimod is a synthetic Toll-like receptor 7 agonist that acts as an immune response modifier and is currently used to treat genital warts, superficial basal cell carcinoma, and actinic keratosis. In a mouse model, the immunogenicity of influenza vaccine was enhanced by applying imiquimod cream, the local immune-boosting effects indicate that imiquimod can be potentially used as vaccine adjuvant to improve immunogenicity (Zhang et al., 2014). In a clinical trial in elderly subjects, pre-treatment with topical imiquimod significantly expedited, augmented, and prolonged the immunogenicity of influenza vaccination relative to a vaccine-only group, with earlier and better seroconversion rate sustained to 1 year, and fewer hospitalizations for influenza or pneumonia (Hung et al., 2014). In a phase 2b/3 trial, topical application of imiquimod before intradermal trivalent influenza vaccine significantly improved immunogenicity against the vaccine influenza strains in young healthy individuals and increased immunogenicity against the non-vaccine strains (Hung et al., 2016). Performing such pre-treatment along with vaccination is, however, inconvenient in a clinical setting and compromises adoption of the process. This is particularly true in mass vaccination-programs, and is further complicated when additional benefit can be realized by maintaining the pre-treatment pharmaceutical at or near the injection site for a prolonged period of time following immunization.

Thus, there is still a need for safe and convenient devices and methods that enhance the effectiveness of intradermal vaccinations.

SUMMARY OF THE INVENTION

The inventive subject matter provides apparatus, systems and methods in which an occlusive dressing is provided for delivery of topical medication that enhances the effect of an immunizing composition delivered by injection. The occlusive dressing includes a barrier that covers the applied topical medication and a central opening through which an immunizing injection is administered. The topical medication can be applied to the surface of the skin prior to application of the occlusive dressing or applied to a skin-facing surface of the occlusive dressing. The occlusive dressing can be constructed in layers, and include a frame layer and a barrier layer. In some embodiments the occlusive dressing can include a portion that covers the central opening following administration of the injection. The occlusive dressing can include a wound dressing positioned to cover the injection site following immunization. In some embodiments the occlusive dressing can be held in place by a separate wound dressing. Embodiments of the inventive concept can include a measuring device for aliquoting a desired amount of the topical medication. Such a measuring device can be utilized to apply or spread the topical medication.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1 schematically depicts a front view of a device of the inventive concept (i.e. a Vaccine-Grid™)

FIG. 2 schematically depicts a cross section of the device shown in FIG. 1, demonstrating laminar construction.

FIG. 3 schematically depicts an exploded view of the device of FIG. 1. All the four layers are aligned to the center of the device.

FIG. 4 depicts a procedure for using a device of the inventive concept in an immunization process.

FIG. 5A and FIG. 5B schematically depict an alternative embodiment of the device having an attached "wing" portion that can act as a dressing or bandage. FIG. 5A schematically depicts a front view of the device. FIG. 5B schematically depicts an exploded view of the device.

FIG. 6 depicts positioning of adhesive layers in a device of the inventive concept as shown in FIGS. 5A and 5B.

FIG. 7 depicts a procedure for using a device of the inventive concept with a dressing.

FIGS. 8A to 8D: FIG. 8A shows an alternative embodiment of a device of the inventive concept that is configured for use with external bandage. FIG. 8B shows an exploded view of such a device. FIGS. 8C and 8D schematically depict steps of a method for using such a device with an external bandage.

FIG. 9: FIG. 9 depicts an embodiment of a measuring and application tool for use with other devices of the inventive concept.

FIG. 10A schematically depicts a method for using an applicator as shown in FIG. 9. FIG. 10B provides a stepwise series of photographs (I to VI) showing use of an applicator of the inventive concept with an occlusive film.

FIGS. 11A and 11B depict examples of kits of the inventive concept. FIG. 11A depicts a kit that includes instructions for use of a simplified version of a device of the inventive concept. FIG. 11B depicts a kit that includes instructions for use of a topical medication measuring device and applicator and for use of a vaccine-enhancing device of the inventive concept.

DETAILED DESCRIPTION

Figure 1:
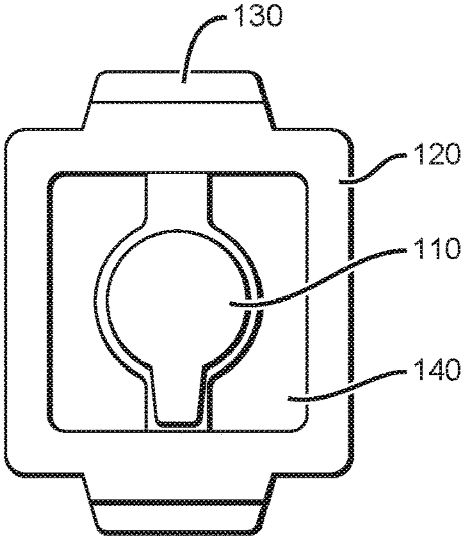
FIG. 1.

The inventive subject matter provides apparatus, systems and methods in which an occlusive device or dressing that includes an access feature is provided that applies a desired amount of an immunization-enhancing formulation (for example, a toll-like receptor 7 agonist, and/or toll-like receptor 9) to an area of skin that is to receive an intradermal vaccination. After a suitable period of time the access feature is utilized (for example, by opening or removal) to permit access to an area of the skin surface for delivery of the intradermal vaccination. In some embodiments a portion of the occlusive device (for example, a "wing") can be deflected to provide a dressing over this access feature following immunization. In other embodiments a dressing can be provided as a separate item. After another suitable period of time (for example, a period of time suitable for providing an enhanced post-immunization enhancement) the device can be removed. The occlusive device can be configured to provide an immunization-enhancing formulation to the immunization site, to a region surrounding the immunization site, or both. In some embodiments the device is self-adhesive to the skin surface. In other embodiments the occlusive device can be applied and/or affixed to the skin surface using a second device (for example, a bandage or dressing).

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

One should appreciate that the disclosed techniques provide many advantageous technical effects including providing methods and devices that increase the effectiveness of intradermal vaccinations in a manner that is safe, convenient, and readily useable in a clinical setting (particularly mass vaccination programs). In some embodiments an intradermal vaccination can be performed prior to or after the topical application of the immunization enhancing pharmaceutical is applied to the skin. It should also be appreciated that in methods and devices of the inventive concept the injection site can be isolated from the topical composition, and therefore can be kept sterile during and after the intradermal injection process. In addition, topical compositions including the immunization enhancing pharmaceutical can be protected from clothing and the environment, permitting them to be retained for an extended time after injection until desirable immunogenicity achieved.

While discussion within this application may focus on vaccination against influenza, the inventors contemplate that devices and methods of the inventive concept can be used with any vaccine composition suitable for subcutaneous, intradermal, subdermal, intramuscular, and/or intravenous use. Such vaccines compositions can be directed to a pathogen such as a virus, bacteria, fungus, and/or parasite. Suitable viral vaccines can be directed to an influenza virus, a hepatitis virus (such as hepatitis A and/or hepatitis B), and/or a virus that causes respiratory infections. In a preferred embodiment the viral vaccine is directed to an influenza virus. In some embodiments the applied vaccine composition can be directed to a disease not caused by a discrete pathogen. For example, devices and methods of the inventive concept can be applied to therapeutic vaccines utilized in the treatment of cancer. Devices and methods of the inventive concept can also be utilized in the application of pharmaceutical formulations that are useful in the treatment of diseases that are responsive to and/or require immune modulation. Such diseases include allergy, multiple sclerosis, and Alzheimer's disease.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The present invention provides occlusive devices and methods that enhance the effects of immunization. This is accomplished by providing an occlusive device that simplifies safe and effective topical application of a composition containing an immunization enhancing pharmaceutical at or near (e.g. surrounding) a vaccine injection site. Such an immunization enhancer can be an aluminum-based salt, such as alum, aluminum phosphate, and/or aluminum hydroxide. In some embodiments an immunization enhancer can be an organic compound, such as a squalene. In some embodiments a suitable immunization enhancer can be a toll like receptor agonist, such as a toll like receptor 7 agonist and/or a toll like receptor 9 agonist. In a preferred embodiment the immunization enhancer can be imiquimod. To avoid the potential infection during injection and permit time for tissue penetration, the topical composition is preferably applied on and/or around the vaccination site for a period of time (for example, 1 to 2 hours) prior to the vaccine injection, and can require protection from clothing, accidental contact, and other environmental factors during this period.

In practice this process is time-consuming and error-prone. Proper application can require the additional step of cleaning the residual topical composition from the site before injection, and can suffer from lack of compliance (even from medical professionals). For example, early removal of the topical composition containing the immunization enhancer (for example, due to limited personnel in a clinical setting) can compromise the immune-boosting effects on immunogenicity.

In some embodiments of the inventive concept, an applicator that can deliver a fixed or selectable volume of a topical formulation (for example a cream, powder, paste, ointment, lotion, liquid, suspension, foam, and/or gel) onto at least a portion of a device of the inventive concept that is subsequently brought into contact with a skin surface that is intended for use in immunization. Alternatively, skin at or around the intended immunization site of the individual to be immunized can supplied with such a volume of topical formulation. The fixed volume of the topical formulation can be from 25 μL to 4 mL. The volume of topical formulation can be selected to provide adequate coverage at and/or around an immunization site so as to enhance the immune response to the supplied immunogen. It should be appreciated that the volume of the topical formulation can be varied to accommodate the nature of the vaccine and/or characteristics of the individual to be immunized (for example, age, gender, size, body composition, underlying health conditions, previous disease status, etc.). In some embodiments the topical formulation can be supplied as part of the device, for example as a pre-applied layer that is brought into contact with the skin on application. In such embodiments dosing of the topical formulation can be controlled or adjusted by selection of a device of appropriate size. Alternatively, in some embodiments the topical formulation can be supplied as a pre-filled dose or bolus that is expressed onto an applicator and/or onto an area of the skin of the subject to be immunized. In some embodiments such an applicator can be sized to provide a desired amount of topical formulation, and/or can include indicia that permit a user to select a desired amount of topical formulation.

Devices and methods of the inventive concept can utilize or support the use of a formulation that includes toll like receptor 7 agonists and/or toll like receptor 9 agonists as immune enhancers. Suitable toll like receptor agonists include imidazoquinoline derivatives (e.g. imiquimod and/or resiquimod), guanosine analogs (e.g. loxoribine), pyrimidine analogs (e.g. bropirimine), phosphonic acid derivatives, and 8-oxoadenine derivatives and their carboxylate esters. In a preferred embodiment the immune enhancer is imiquimod, which can be provided as a topically applicable lotion, cream, or gel. Such an immune enhancer can be supplied in an applicator that is used in conjunction with a device of the inventive concept, or can be incorporated into one or more skin-contacting portions of the device as supplied.

Topical composition suitable for use with occlusive devices of the inventive concept can include an immunization enhancing pharmaceutical (such as imiquimod) that can be applied to an area at and/or near the sited of vaccination. In some embodiments of the present invention, the occlusive device provides or is supplied with dispensing or measuring device that includes a reservoir sized to include a suitable amount of the topical composition (for example, from 1 cm to 10 cm×1 cm to 10 cm) that surrounds the intended site of vaccination following application to an individual to be vaccinated. The reservoir area for the topical composition can have a shape that covers an area greater that 1 $cm^2$, for example up to 8 $cm^2$ or more. Such a reservoir can have any suitable configuration. For example, such a reservoir can be circular, ovoid, square, rectangular, polygonal, and/or irregular. Such a reservoir can have a minimum dimension of about 1 cm and a maximum dimension of up to 8 cm. The reservoir can be made from any suitable material that is not reactive with the pharmaceutical stored therein, for example a polymer such as polyethylene, polypropylene, or silicone. In some embodiments the reservoir can include additional features to enhance the stability of the immunization enhancing pharmaceutical, for example impermeability to oxygen, ability to block UV and/or visible light, etc.

Embodiments of the inventive concept can include an adhesive-bearing portion that permits the occlusive device to cling to the skin during use. In some embodiments the adhesive-bearing portion is coupled to the reservoir. In other embodiments the adhesive-bearing portion is provided as a separate piece, for example as a tape or bandage that is applied to the reservoir on use. An adhesive-bearing portion can be made of any suitably flexible and supportive material, such as a polymer sheet, a polymer mesh, a woven fabric (natural or synthetic), or a nonwoven fabric (natural or synthetic). In a preferred embodiment at least a part of the adhesive-bearing portion permits the free passage of air (i.e. is breathable) in order to promote comfort and skin integrity when the device is in use. The adhesive-bearing portion can include a surface that is applied to the skin when in use. At least a portion of this skin-facing surface can include a pharmaceutically compatible adhesive that provides a transient bond to skin surface. Such a transient bond should be stable for from 5 minutes to up to 48 hours following application to the skin. In some embodiments the occlusive device can be provided with a removable (e.g. peelable) cover that protects this adhesive prior to application.

Some embodiments of the inventive concept incorporate a bandage or dressing, which can be used to cover the puncture wound resulting from vaccination. Such a bandage or dressing can be coupled to or provided by a portion of the device. For example, a device of the inventive concept can include a tab or wing that can be folded over to act as a bandage or dressing. In other embodiments a bandage or dressing can be provided as a separate item that is applied following immunization. Such a bandage or dressing can include an adhesive portion, and absorbent portion, and a backing. The backing can be made from any suitably flexible material, for example a polymer sheet, polymer mesh, woven fabric, unwoven fabric, etc. The absorbent portion can be coupled to the backing and include a material suitable for absorbing and/or containing blood and other body fluids. Suitable absorbent materials include a fabric, wool, and/or gel made of natural or synthetic materials. In some embodiments the absorbent material can include an agent that provides pain control (such as a topical analgesic or anesthetic) and/or promotes healing (such as an antibiotic). The adhesive portion can be an adhesive layer that is coupled to the backing. Such an adhesive layer can be provided as an adhesive compound applied to at least a portion of the backing or as a layer of material that incorporates such an adhesive compound and is coupled to the backing.

Some embodiments of the inventive concept can include a dispensing or measuring device suitable for storing and dispensing the topical composition. Such a device can be provided as reservoir dimensioned to accommodate at least a volume of the topical composition suitable for a single use. Such a reservoir can be reversibly sealed, for example using a polymer film or sheet that is reversibly affixed to an opening of the reservoir. Such a dispensing device can include an applicator, which facilitates removal of the topical composition from the reservoir and application to the skin of a subject in need of immunization or to a skin-contacting surface of a device of the inventive concept. In some embodiments such an applicator can include indicia (for example, visible lines or similar symbols along its length) that permit metering or measurement of the amount of topical composition present on the applicator.

An example of an occlusive device of the inventive concept is shown in FIG. 1. As shown, the occlusive device provides an occlusive dressing that protects and maintains a layer on the skin of a medicament that enhances immune response to an injected vaccine. The occlusive device provides a through-hole through which the vaccination can be administered. The example shown in FIG. 1 provides a frame (120) that supports a film (140) which serves to protect the layer of medicament. The frame (120) can be constructed of any suitable paper (for example, cardboard, fiberboard, etc.) or polymer (for example, polyethylene, polypropylene, nylon, silicone, etc.), and have sufficient thickness to support the film (140) and other elements of the occlusive device while being sufficiently pliant for application to a skin surface. The film can act as a barrier layer during use of the occlusive device. In some embodiments the frame (120) can include or support one or more tabs (130), which can serve to improve adhesion to the skin surface. The film can be made from a suitable polymeric material (e.g. polyethylene, polypropylene, nylon, silicone, etc.) that provides an environmental barrier (e.g. resistance to moisture, etc.), and in preferred embodiments is transparent or translucent. The frame (120) can support a through hole cover (110), which serves to cover a through-hole that extends through the occlusive device. Such a through-hole can be produced by the alignment of apertures in different portions of the occlusive device.

In some embodiments occlusive devices of the inventive concept are constructed in a laminar or layered fashion. This can be seen in FIG. 2, which depicts a cross section of an occlusive device such as that shown in FIG. 1. As shown the occlusive device is constructed of a number of layers, including a through-hole cover 110, a frame 120, a film (140), and a backing (150). Each of these layers can be constructed of a different material. Layers of the occlusive device can be joined by any suitable means. For example, layers can be joined using an adhesive, by melting, by welding (e.g. ultrasonic welding), by crimping or folding, and/or by using joiners (e.g. stitching, stables, etc.). In some embodiments the connection between two or more layers can be readily disrupted without the use of tools (e.g. a "peelable" layer), permitting removal of or disconnection or a portion of one or more layers from the bulk of the occlusive device. Such laminar construction facilitates manufacture of the occlusive device.

Figure 3:
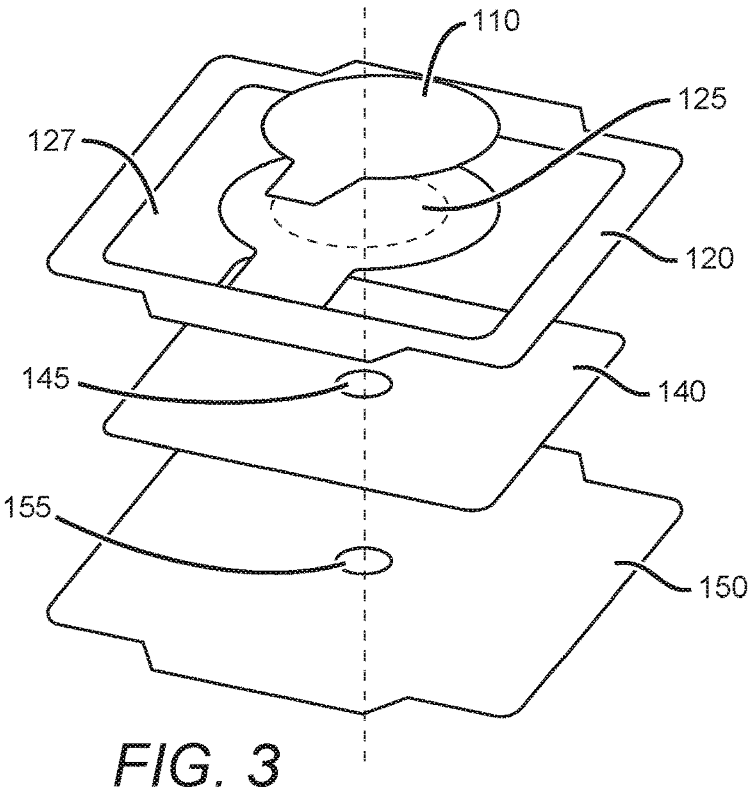
FIG. 3.

FIG. 3 provides an expanded view of an occlusive device as shown in FIG. 1. As shown, the through-hole cover (110) is centered over frame aperture (125) that is at least approximately centrally located on the frame (120). The frame aperture (125) can be defined by a ring or similarly shaped portion that extends from an interior edge of the frame (120). Remaining open space between the edges of the frame (120) define a frame cutout (127) through which the film (140) can be seen. As shown the film (140) includes a film aperture (145) that is in central alignment with the frame aperture (125). The backing (150) similarly includes a backing aperture (155) that is centrally aligned with the frame aperture (125) and the film aperture (145). This alignment of apertures in the assembled occlusive device provides a through-hole through which the vaccination is administered.

In some embodiments the backing (150) can include an adhesive on the side facing away from the film (140), which can aid in adhering the occlusive device to the skin during use. In such embodiments this adhesive can be covered by a removable or peelable film. In other embodiments the backing (150) can be removed prior to use to expose the surface of the film (140) facing away from the frame (120). In such embodiments the film (140) can include an adhesive interposed between the film (140) and the backing (150) that aids in affixing the occlusive device to the skin of a patient to be immunized. Alternatively, the film (120) can be constructed of a material having sufficient taction to cling to the skin without the need of an adhesive.

In some embodiments of the inventive concept the occlusive device can be provided with a medicament that enhances immune response to a vaccination already incorporated into the occlusive device. For example, such a occlusive device can include a layer of the medicament interposed between the film (140) and the backing (150), such that removal of the backing exposes the medicament. Alternatively, the backing (150) can include a layer of medicament applied to the surface facing away from the film (140). Such a layer can be covered with a removable barrier during storage, which is removed upon application to a patient. In other embodiments the medicament is provided in a separate container or applicator.

Figure 2:
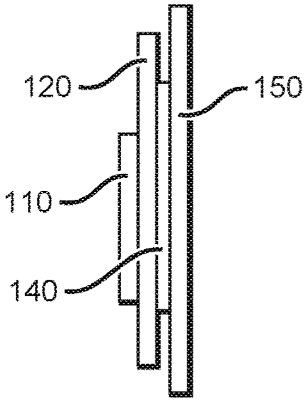
FIG. 2.
Figure 4:
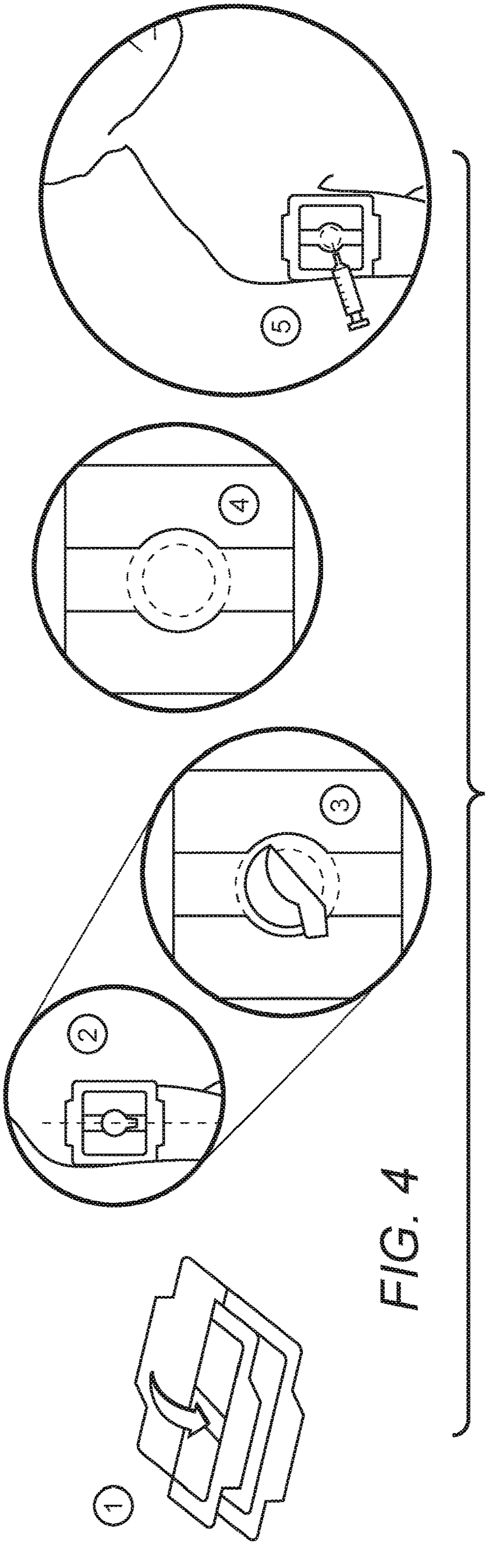
FIG. 4.

FIG. 4 illustrates a method for using an occlusive device such as that shown in FIGS. 1 to 3. From left to right, a backing is removed from the underside of the occlusive device (1), which is then applied to a suitable immunization area with the through-hole cover oriented away from the skin (2). In this instance the upper arm is shown, however other sites are suitable. Occlusive devices of the inventive concept can be supplied in various sizes (e.g. from 4 cm×4 cm to 10 cm×10 cm) and configurations (e.g. square, rectangular, circular, ovoid, etc.) adapted to different immunization sites and/or different patient sizes. In some embodiments a medicament that enhances immune response to a vaccinating composition is applied to the skin prior to application of the occlusive device. In other embodiments such a medicament is incorporated into the occlusive device and is applied to the skin on application. The occlusive device can be left in place on the skin for a period of time sufficient for the medicament to provide the desired enhancement on administration of the vaccine (e.g. from 30 seconds to 48 hours) or, alternatively, the vaccine can be given immediately.

In order to administer the vaccine the through-hole cover is removed (3) to expose the area of skin where the immunization is to be administered (4). At this point a topical analgesic can be applied to this exposed area, if desired. In some embodiments the lower surface of the through-hole cover can include a topical anesthetic, such that the anesthetic is applied to the immunization area on application of the device. Finally, the immunization is administered (for example, by microneedle, intradermal, subdermal, or intramuscular injection). Following administration of the vaccine the occlusive device can be kept in place for a period of time suitable to enhance the immune response to the injection (e.g. from 5 minutes to 48 hours). In some embodiments a portion of the occlusive device can be removed. For example, the frame can be removed while leaving the film layer in place on the patient. Alternatively, if the occlusive device has been applied for a period of time prior to administration of the vaccine sufficient to enhance its effect, the occlusive device can be removed essentially immediately following administration.

Figure 5A:
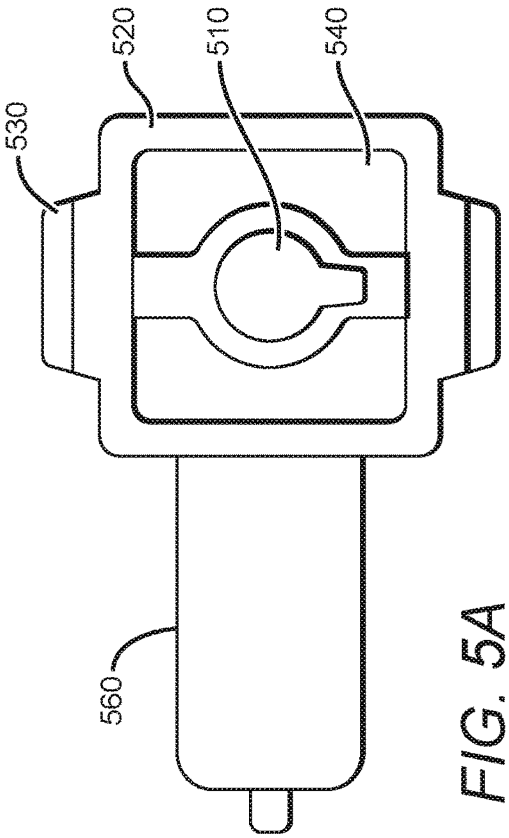
FIGS. 5A and 5B.
Figure 5B:
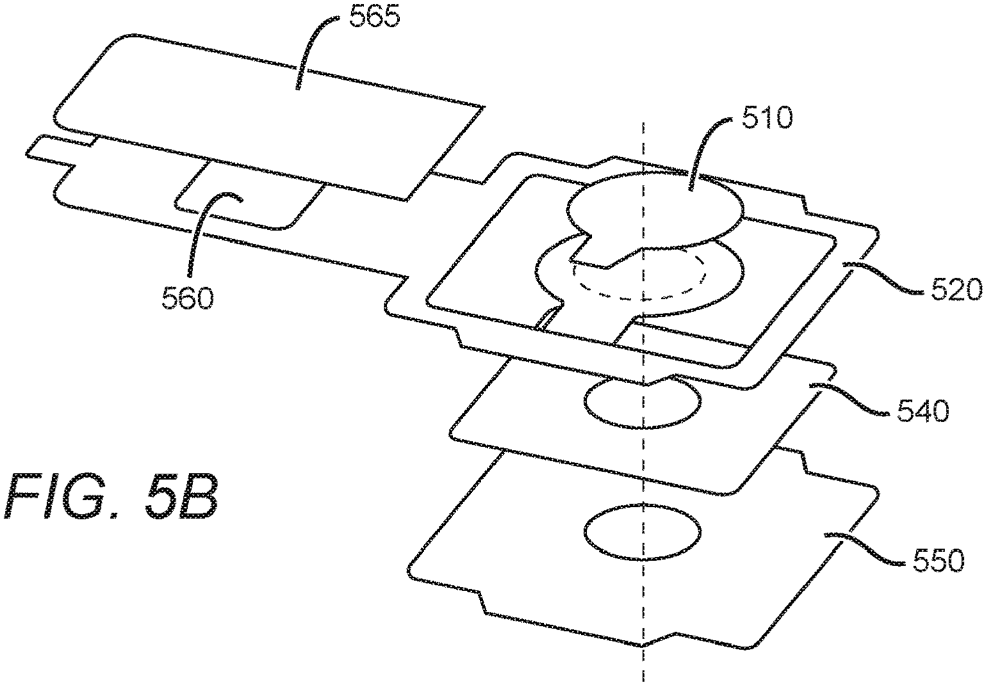

Vaccination by injection necessarily leaves a skin wound, which can bleed or become infected. Accordingly, some embodiments of the inventive concept incorporate or support the use of a wound dressing. FIG. 5A depicts an embodiment of the inventive concept in which the occlusive device includes a wound dressing (560). Other portions of the occlusive device can be similar to those of the occlusive device in FIG. 1, including a frame (520), a through-hole cover (510), and a film (540). In some embodiments one or more tabs (530) aid in holding the occlusive device in place while in use. The film (540) can act as a barrier layer during use of the occlusive device. The wound dressing (560) can be attached to or extend from an outside edge of the frame (520), film (540), or any portion of the occlusive device that is retained on the skin during use. FIG. 5B provides an expanded view of the device of FIG. 5A. As shown the wound dressing (560) can include a dressing protective film (565) that is removed prior to application of the dressing. The wound dressing (560) can include an adhesive layer that is covered by the dressing protective film (565) during storage. As shown, the through-hole cover (510) is positioned to occlude a through-hole produced by the superimposition of apertures in the frame (520), film (540), and backing (550) during storage. In the embodiment shown the wound dressing (560) is attached along one edge to an outer edge of the frame (520), which permits it to be deflected over the through-hole following immunization.

Figure 6:
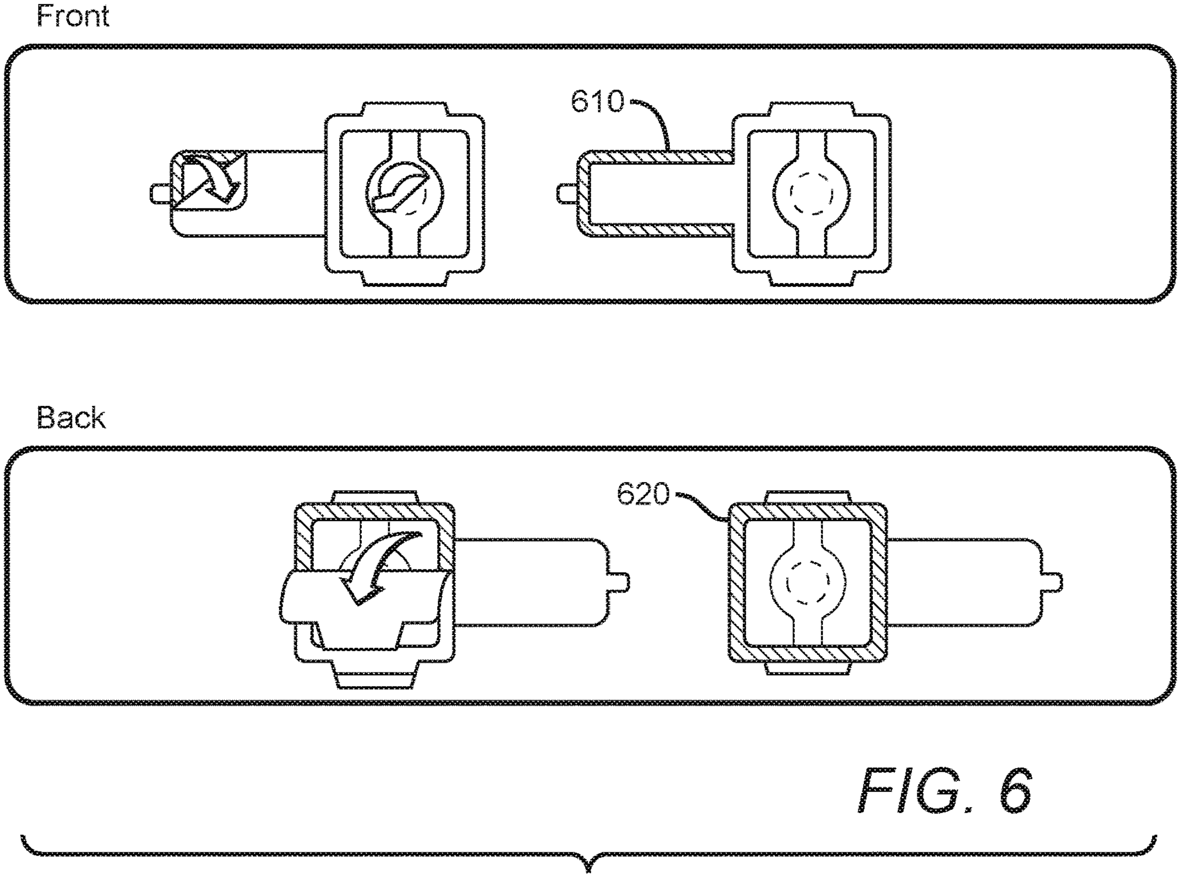
FIG. 6.

As noted above, occlusive devices of the inventive concept can include one or more adhesive layers, strips, or patches that aid in positioning and use of the device. Such adhesive layers, strips, or patches can be covered by removable films that provide protection during storage and prior to use. FIG. 6 shows and example of the positioning of such adhesive portions in an occlusive device as shown in FIGS. 5A and 5B. The upper panel shows a view of the "front" (i.e. oriented away from the skin during use) of the occlusive device, where removal of a peelable film exposes a layer of adhesive used to secure the wound dressing (610). The lower panel shows a view of the "back" (i.e. oriented towards the skin during use) of the occlusive device, where removal of a peelable film exposes a layer of adhesive (620) that aids in fixing the occlusive device to the skin surface.

Figure 7:
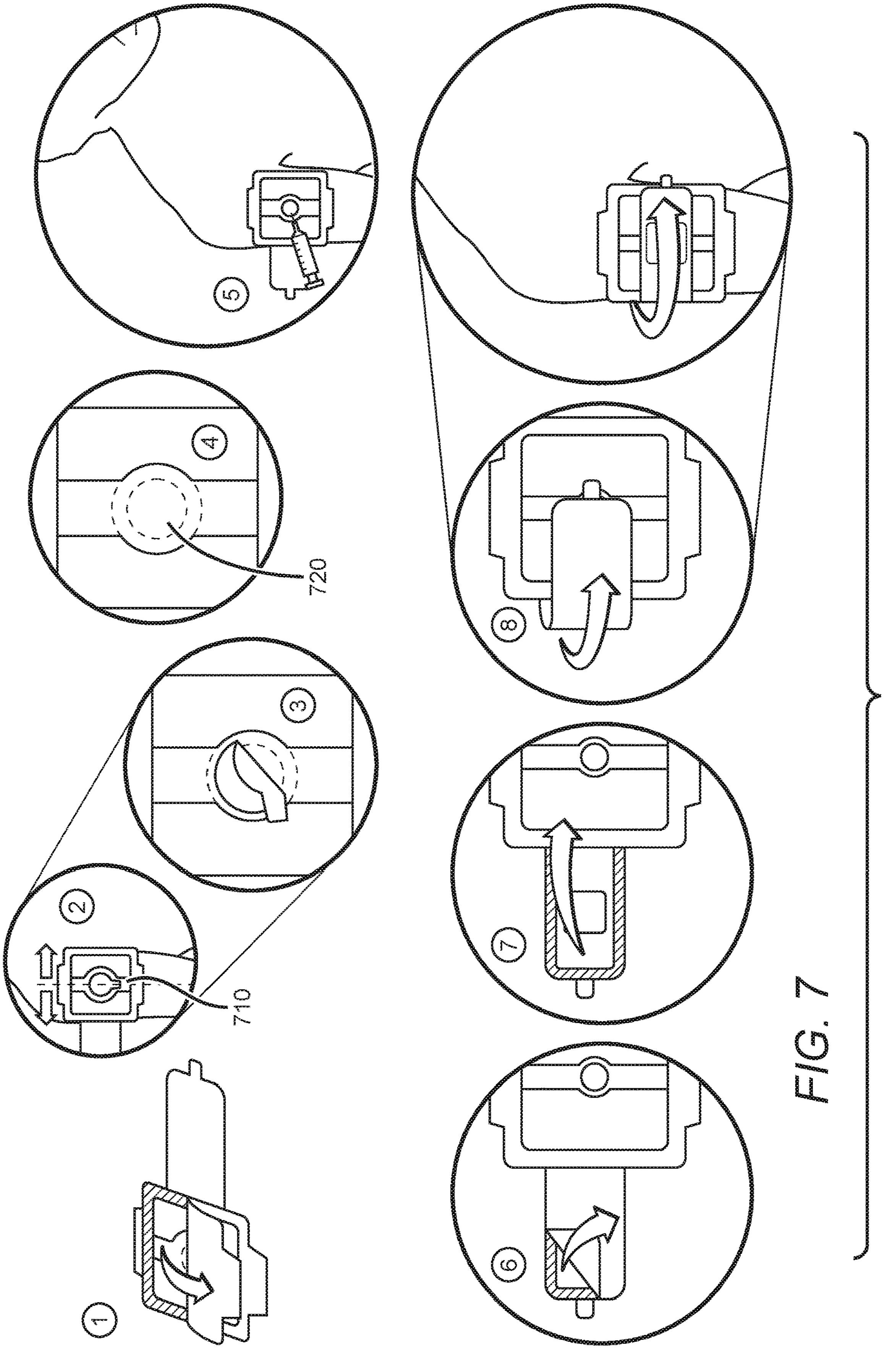
FIG. 7.

FIG. 7 depicts a method for using an occlusive device of the inventive concept that incorporates a wound dressing (such as the occlusive device shown in FIGS. 5A and 5B). From left to right, a peelable film is removed from the back of the occlusive device (1), after which the device (710) is affixed to the skin such that the through-hole is oriented over the desired immunization site (2). As noted above, a medicament that enhances the immune response to the vaccine to be administered can be placed on the skin prior to application of the occlusive device. Alternatively such a medicament can be incorporated into the occlusive device such that it is applied to the skin on placement. In some embodiments the occlusive device can be left in place for a period of time in order for the medicament to take effect, as noted above. In order to administer the vaccine the through-hole cover is removed (3), and a topical anesthetic can optionally be applied to the vaccination site (4), through the through-hole (720). As noted above, in some embodiments a topical anesthetic can be provided on the skin-facing surface of the through-hole cover. Following removal of the through-hole cover the vaccine can be injected (5). Following injection the wound dressing can be prepared for use by removal of a film protecting the wound-facing surface (6). The wound dressing can then be placed over the wound produced by vaccination, for example by folding over at or near an area where it is joined to the bulk of the device (7, 8). An adhesive layer applied to at least a portion of the skin-facing surface of the wound dressing can serve to keep it in place until the device is removed (for example after a period of time sufficient for the medicament to have the vaccination-enhancing effect, as described above).

Figure 8A:
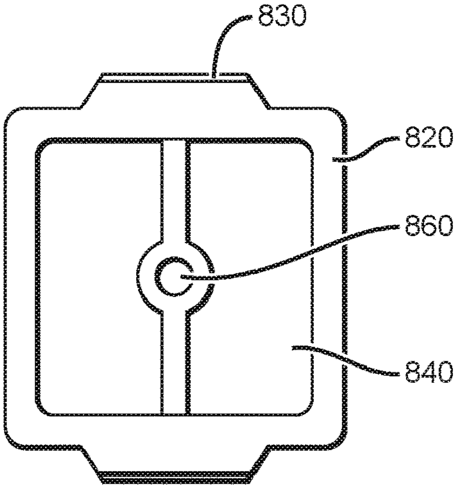
Figure 8B:
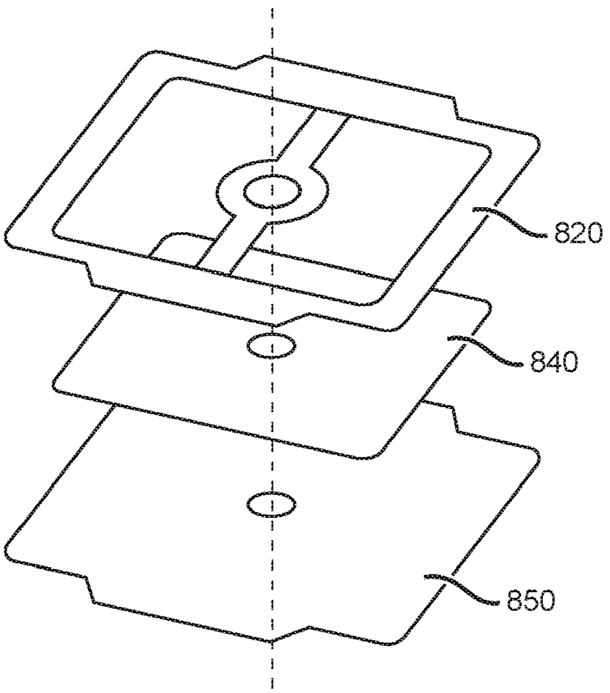

FIG. 8A depicts an alternative, simplified occlusive device of the inventive concept. Such a simplified occlusive device is suitable for use with a separate wound dressing or bandage, and can be manufactured at low cost. As shown the occlusive device includes a frame (820) that can support one or more tabs (830), and also includes a film (840) and backing (not shown in this view). The film (840) can act as a barrier layer during use of the occlusive device. Alignment of apertures in these layers provides a through-hole (860). FIG. 8B provides an expanded view of the simplified occlusive device, and shows the arrangement of the frame (820), film (840), and backing (850) portions. As noted above, such an occlusive device can incorporate a medicament that enhances immune response to a vaccine composition that is positioned so that it is brought into contact with the skin during use (for example, on a skin-facing surface of the backing or film). In other embodiments such a medicament is provided from a separate source prior to application of the occlusive device.

Figure 8D:
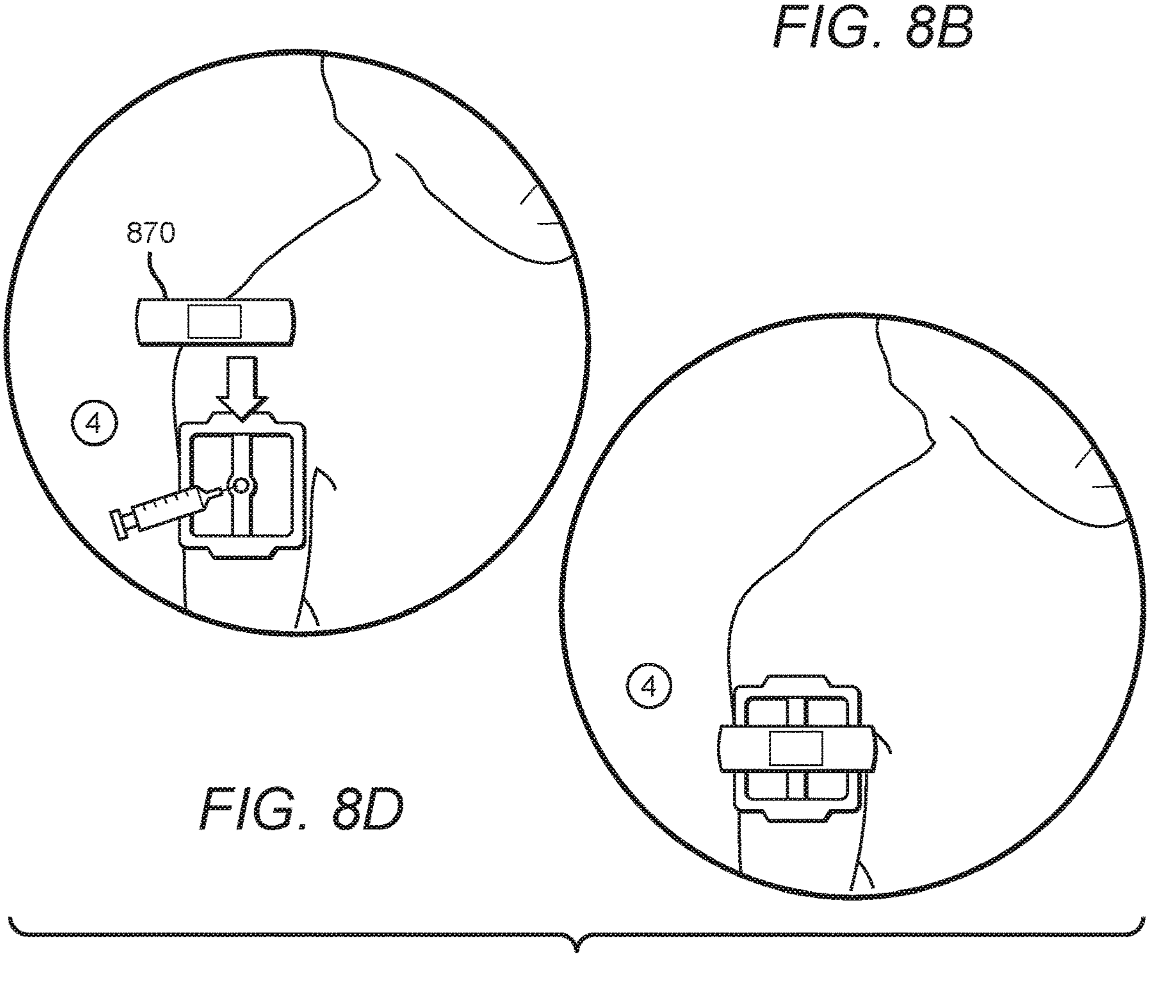

FIG. 8C illustrates a method for using a simplified occlusive device such as that depicted in FIGS. 8A and 8B. From left to right, a protective film is removed from the device (1) and the occlusive device is oriented over and affixed to the skin such that the through-hole lies over the desired vaccination site (2). A topical anesthetic can be applied to at least a portion of the area of skin exposed by the through-hole prior to vaccination (3). As noted above, a medicament that enhances the immune response to vaccination is applied to the skin either on application of the occlusive device (e.g. where the medicament is provided with the occlusive device) or prior to application of the occlusive device. The occlusive device can then be kept in place for a period of time that permits the medicament to enter tissues at or near the vaccination site. Alternatively, vaccination can be performed essentially immediately and the occlusive device maintained in place afterwards (as described above). Vaccination can be accomplished by injection (4). Additional optional steps are shown in FIG. 8D, where following injection (4) a wound dressing (870) is applied to the wound created by injection. Such a wound dressing can, advantageously, aid in holding the occlusive device in place following vaccination. As noted above, in some embodiments a portion of the occlusive device (e.g. the frame) can be removed during use while maintaining a remaining portion (e.g. the film) in contact with the skin.

As noted above, in some embodiments a topical medicament is provided as part of the occlusive device that acts to enhance the immune reaction to the vaccine composition. In other embodiments the medicament is provided as a separate portion. In such embodiments it is advantageous to be able to dispense a predetermined or desired portion or dose of the medicament rather than rely on estimation of the amount applied by a health care professional. FIG. 9 depicts an example of such a measuring or portioning device. Such a measuring device can have a laminar construction. As shown the measuring device has a base (930) with a reservoir (940), which can be produced by indenting a portion of the base. Alternatively the reservoir (940) can be a distinct feature that is joined to the base (930), for example by gluing, melting, or welding. In some embodiments the reservoir can serve as part of a repository for a portion of topical medicament (950), which can reside in the measuring device until use. In other embodiments the reservoir provides a defined volume into which a portion of medicament is introduced prior to use. The base (930) can be made of any suitable material, such as a metal foil or polymer sheet. The base (930) can be joined to a plate (920), which provides structural support. The plate (920) includes a plate aperture (925) that is aligned with the reservoir (940). The reservoir (940) is sealed by a removable film (910), which can be removably attached to the plate (920). The removable film (910), plate (920), and base (930) can be joined by any suitable method, including the use of an adhesive, melting, welding, and fixing devices.

Figure 10A:
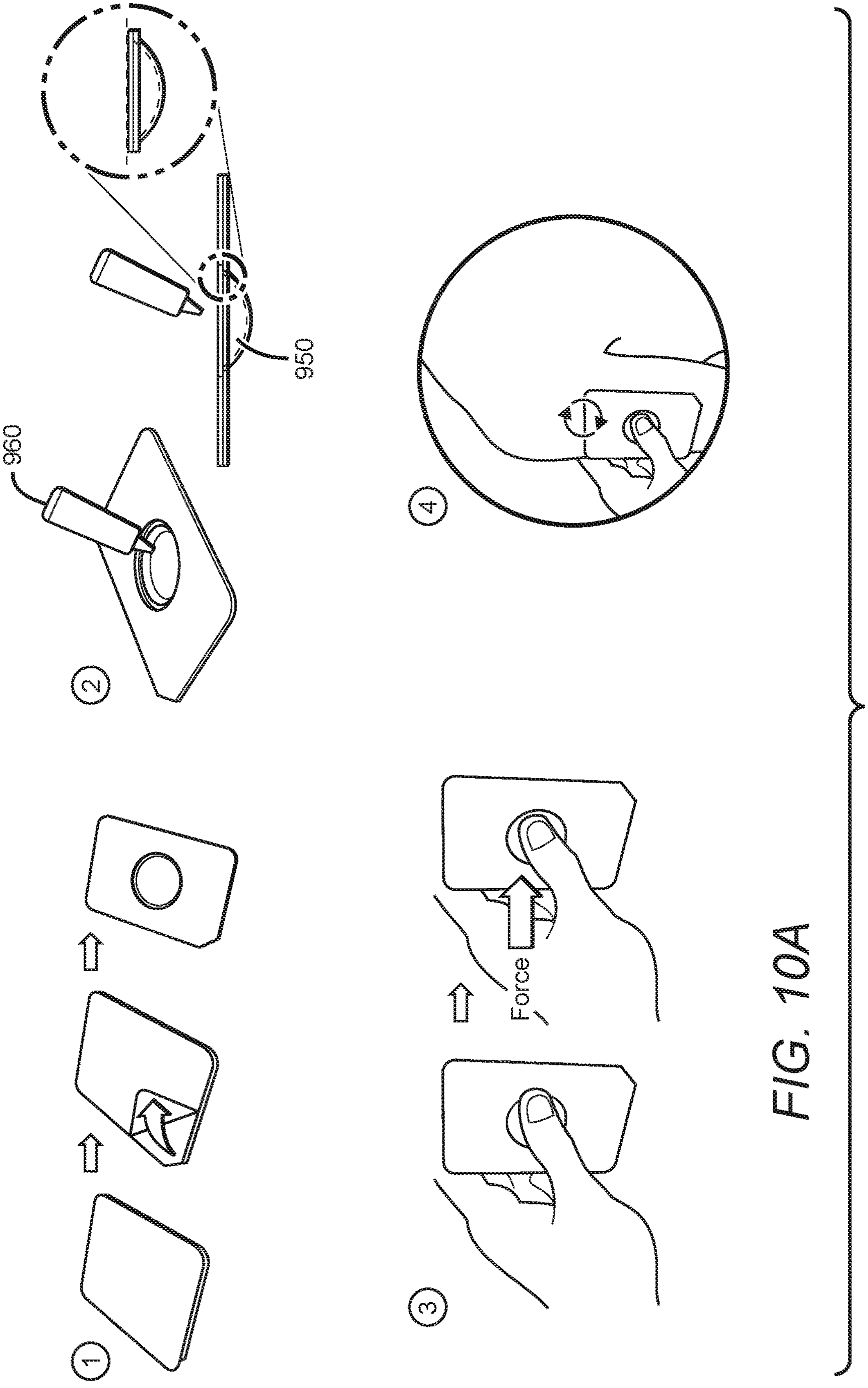
FIGS. 10A and 10B.

FIG. 10 depicts a method of using a measuring device as shown in FIG. 9 with a separate supply of a topical medicament. From left to right, the removable film is peeled away to expose the reservoir (1). A dispenser (960) of the topical medicament is used to place a portion of the medicament in the reservoir (2), which provides a defined volume that represents a desired unit dose of the topical medicament. It should be appreciated that the reservoir can have any suitable shape, including a hemisphere, ovoid, or polygonal volume. The volumes of such shapes are readily calculable from known geometric formulae. To dispense the topical medicament a healthcare professional can exert pressure on a protruding portion of the reservoir until it reverts (3). The exposed portion of topical medicament can then be applied to the skin surface (4). Flat surfaces of the measuring device can be utilized to spread the topical medicament and avoid contamination of the healthcare professional's hand.

Figure 10B:
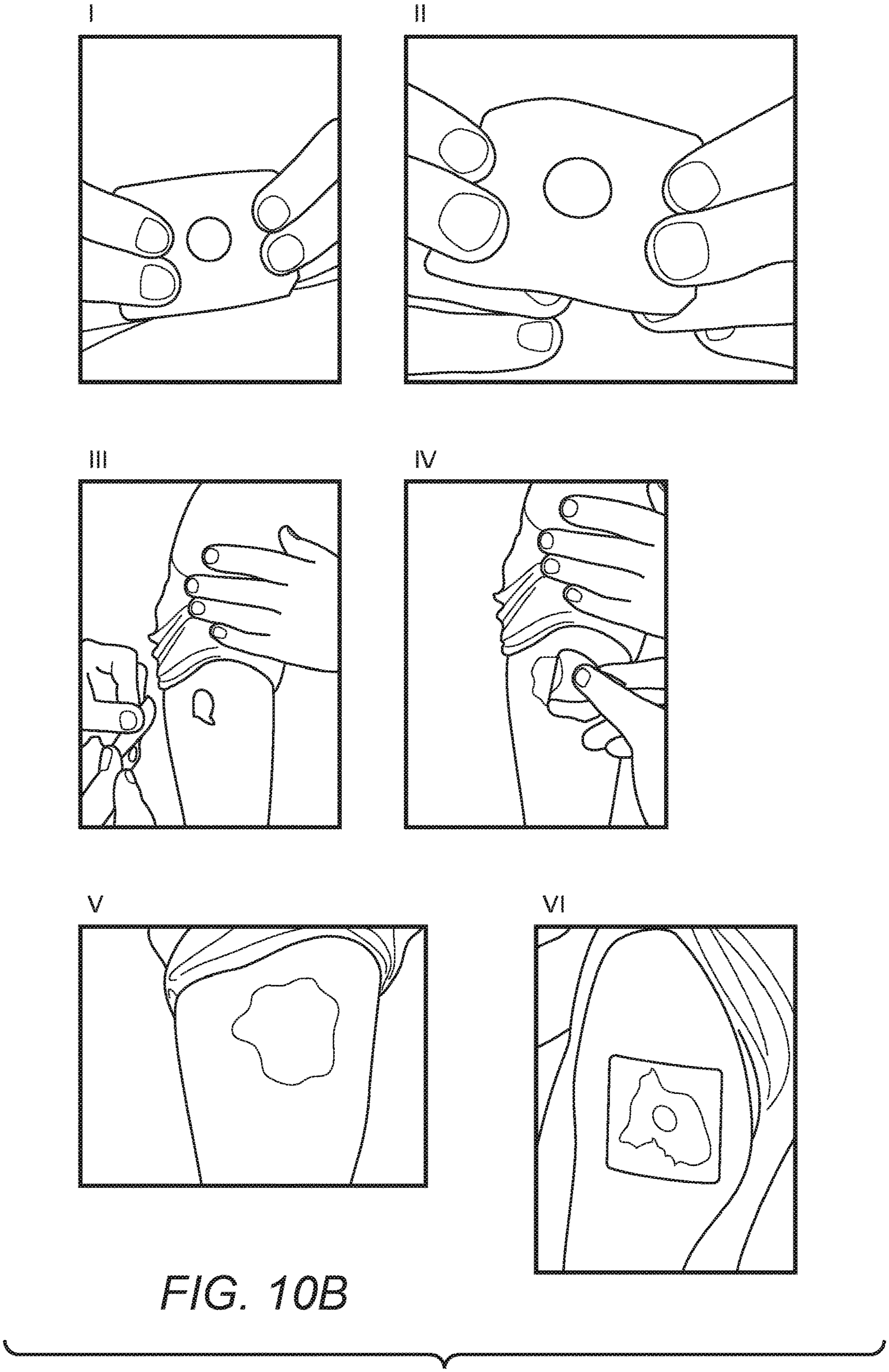

In some embodiments, a measuring device can be used independently of an occlusive device of the inventive concept. As shown in FIG. 10B, the reservoir portion of a measuring device can be filled with a topical medicament (I) in order to provide a desired unit dose. This unit dose can be exposed for application by everting the reservoir portion of the measuring device (II). The exposed topical medicament is then applied to the skin surface at or near the intended vaccination site (III) and distributed over the skin (IV). This provides a treated vaccination site (V), which can be protected by the application of a dressing or film (VI) to maintain the topical medicament at the vaccination site for the desired period of time (for example, up to 48 hours). In some vaccination protocols this period of time can be prior to, following, or both prior to and following application of the vaccine to the patient.

Figure 11A:
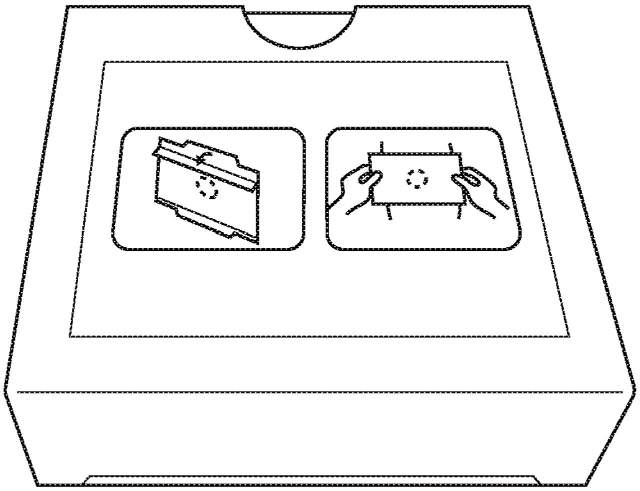
FIGS. 11A and 11B.
Figure 11B:
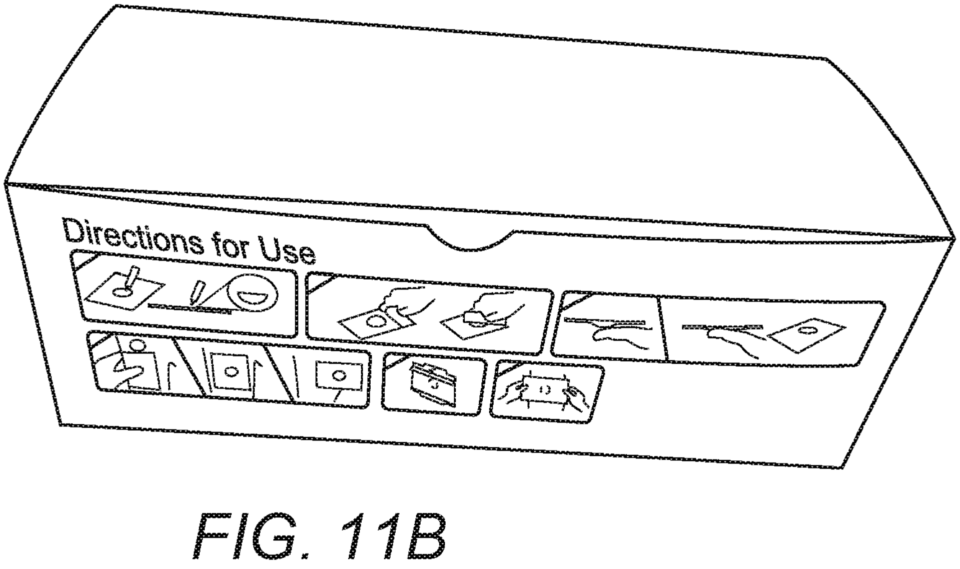

In some embodiments an occlusive device of the inventive concept as described above can be provided as part of a kit. Such a kit can include instructions for use, and can also include a measuring device and/or a supply of topical medicament. In some embodiments a kit can include two or more devices and/or measuring devices. Kit packaging can include indicia suitable for product identification and/or tracking (for example, 1 and 2 dimensional bar codes). Such packaging can also include a memory device (such as an RFID chip) that can store and transmit information related to the package and/or its contents, such as package contents, date of manufacture, expiration date, and so on. In some embodiments packaging for devices of the inventive concept can include indicators that provide indications of exposure to water or moisture, extreme temperatures, and other conditions that may adversely impact contents of the package. FIG. 11A shows a photograph of such a kit, with instructions for use of a simple version of the occlusive device. FIG. 11B shows a photograph of a kit with instructions for use of an occlusive device and of a measuring device.

In a typical vaccination method of the inventive concept, when vaccination is performed using an occlusive device as described above a protective layer is initially remove from the skin-facing surface of the occlusive device. In some embodiments the exposed surface can include a topical preparation of an immunization enhancing pharmaceutical that is deposited during manufacturing, and is exposed by removal of then protective layer. In other embodiments a clinician can apply a topical preparation of an immunization enhancing pharmaceutical following removal of the protective layer. For example, a suitable amount of 5% imiquimod cream (e.g. one containing 12.5 mg of imiquimod in 250 mg of cream) can be evenly spread on the skin facing surface of the occlusive device. Afterwards the occlusive device is placed on the skin of the patient where a vaccine will be administered. In another embodiment, imiquimod cream can be applied directly to the skin of a person to be vaccinated. After a suitable period of time (for example, about 5 minutes) the through-hole cover of the occlusive device is removed. The skin thus exposed can be disinfected (for example, using 75% alcohol) and then the influenza vaccine can administered to the patient intradermally through the exposed opening. In some embodiments a skin facing surface of through-hole cover can include a topical preparation of a local anesthetic, such as lidocaine. Alternatively, as an optional step before intradermal injection, local anesthetic can be applied to the skin at the vaccination site either by injection or pressure gun to reduce pain.

The skin facing surface area of the occlusive device can provide a consistent amount of immunization enhancing pharmaceutical compound, which is evenly and consistently provided to patient skin in each treatment. Use of an occlusive device of the inventive concept simplifies disinfection of the skin at the injection site; as a result the time required for vaccine administration can be shortened, thereby improving the efficiency of the vaccination program. This method can also allow the vaccination enhancing pharmaceuticals to remain on the skin for a defined period of time. Shown below are examples in how a vaccination enhancing pharmaceutical such as imiquimod can be used with the device to enhance the effectiveness of influenza and other vaccinations.

In vaccination using a 2 cm×2 cm sized occlusive device a protective layer on the skin-facing surface of the occlusive device is first removed. Approximately 0.2 mL of 5% imiquimod cream (containing 12.5 mg of imiquimod in 250 mg cream or gel) is applied evenly on to the exposed surface of the occlusive device. The occlusive device is then placed on the arm of the patient, with the vertical axis being aligned with the arm. After a suitable period of time (for example, about 5 minutes), the through-hole cover is removed. The skin exposed is then disinfected and the influenza vaccine is administered intradermally via the exposed through-hole.

As shown above, in some embodiments the occlusive device includes a 'wing' protrusion or attachment that incorporates an elastoplast-like wound dressing or bandage to facilitate the vaccination process. The vaccination procedure as described above can be used to perform vaccination. After the intradermal injection is completed and a 'balloon' or bleb of inoculant is formed under skin has been absorbed, a protective layer can be removed to expose a bandage portion that extends from the main body of the device. This bandage 'wing' can be folded over the main body of the device to cover and protect the injection site.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of applying a topical medication, comprising:

(i) providing an occlusive device comprising a barrier layer, wherein the barrier layer comprises a central aperture and a first surface, wherein the central aperture extends through the first surface, wherein the occlusive device further comprises a frame that is affixed to a second surface of the barrier layer, wherein the second surface is opposite to the first surface of the barrier layer, wherein the frame comprises a frame aperture that is in central alignment with the central aperture of the barrier layer, and wherein the first surface comprises an amount of the topical medication; and (ii) affixing the occlusive device to an area of the skin of an individual in need of treatment, wherein the first surface is in contact with the skin, and wherein the topical medication on the first surface is in contact with the skin, wherein the central aperture of the occlusive device is included therein prior to affixing the occlusive device to the skin, and wherein at least a portion of the area of the skin is exposed through the central aperture.

2. The method of claim 1, wherein the topical medication is applied using an applicator configured to deliver a fixed volume of the topical medication.

3. The method of claim 2, wherein the fixed volume is from 25 μL to 4 mL.

4. The method of claim 1, wherein the topical medication comprises an immunization enhancer.

5. The method of claim 4, wherein the topical medication comprises a squalene.

6. The method of claim 4, wherein the topical medication comprises a toll like receptor agonist.

7. The method of claim 1, further comprising the step of administering a pharmaceutical formulation through the central aperture by injection.

8. The method of claim 7, wherein the pharmaceutical formulation is a vaccine formulation.

9. The method of claim 1, wherein the method further comprises (a) applying the amount of the topical medication to the first surface prior to, during, or after step (i) and prior to step (ii).

10. A method of applying a topical medication, comprising:

providing an occlusive device comprising a barrier layer, wherein the barrier layer comprises a central aperture and a first surface, wherein the central aperture extends through the first surface, wherein the occlusive device further comprises a frame that is affixed to a second surface of the barrier layer, wherein the second surface is opposite to the first surface of the barrier layer, and wherein the frame comprises a frame aperture that is in central alignment with the central aperture of the barrier layer;

applying an amount of the topical medication to an area of the skin of an individual in need of treatment; and affixing the occlusive device to the area of the skin, wherein the first surface is in contact with the skin, wherein the topical medication is applied to the area of the skin prior to affixing the occlusive device thereto, and wherein the topical medication is an immunization enhancer.

11. The method of claim 10, wherein the topical medication is applied using an applicator configured to deliver a fixed volume of the topical medication.

12. The method of claim 11, wherein the fixed volume is from 25 μL to 4 mL.

13. The method of claim 10, wherein the topical medication comprises a squalene.

14. The method of claim 10, wherein the topical medication comprises a toll like receptor agonist.

15. The method of claim 10, further comprising the step of administering a pharmaceutical formulation through the central aperture by injection.

16. The method of claim 15, wherein the pharmaceutical formulation is a vaccine formulation.

* * * * *